United States Patent [19]

Doyle et al.

[11] 4,434,317

[45] Feb. 28, 1984

[54] SEPARATION AND RECOVERY OF UNSATURATED HYDROCARBONS BY COPPER (I) COMPLEXES

[75] Inventors: Gerald Doyle, Whitehouse Station; Roy L. Pruett, New Providence; David W. Savage, Lebanon, all of N.J.

[73] Assignee: Exxon Research and Engineering Company, Florham Park, N.J.

[21] Appl. No.: 492,225

[22] Filed: May 6, 1983

[51] Int. Cl.$^3$ .............................................. C07C 7/156
[52] U.S. Cl. .................................... 585/845; 585/847; 585/849
[58] Field of Search ......................... 585/845, 847, 849

[56] References Cited

U.S. PATENT DOCUMENTS

| | | | |
|---|---|---|---|
| 3,401,112 | 9/1968 | Dunlop et al. | 206/306 |
| 3,517,079 | 6/1970 | Beckham et al. | 260/674 |
| 3,754,047 | 8/1973 | Long et al. | 260/677 |
| 3,755,487 | 8/1973 | Jahnig et al. | 260/677 |
| 4,042,669 | 8/1977 | Johnson et al. | 423/246 |
| 4,048,292 | 9/1977 | Green | 423/415 |
| 4,279,874 | 7/1981 | Doyle | 423/246 |
| 4,385,005 | 5/1983 | Doyle | 585/845 |

OTHER PUBLICATIONS

W. J. Thomas et al., "The Adsorption of Carbon Monoxide . . . ," J. Applied Chem. (London), vol. 15, pp. 17–28. (1965).
W. Partenheimer et al., "The Syntheses of Some New Silver Olefin Compounds . . . ," Inorg. Chem., vol. 11, pp. 2840–2841, (1972).

*Primary Examiner*—Delbert E. Gantz
*Assistant Examiner*—Anthony McFarlane
*Attorney, Agent, or Firm*—James H. Takemoto; Jay Simon

[57] ABSTRACT

Alkenes, alkynes or mixtures thereof are removed from feedstreams by a process which comprises contacting the feedstream with a solution of a cuprous fluorinated acetylacetone in an organic solvent containing stabilizing agent to remove alkene, alkyne or mixture thereof by forming a first cuprous complex, decomposing the first cuprous complex whereby stabilizing agent replaces alkene or alkyne in the first cuprous complex to form a second cuprous complex, and separating the displaced component. The formation of the second cuprous complex avoids any deposition of copper metal upon heating.

12 Claims, No Drawings

SEPARATION AND RECOVERY OF UNSATURATED HYDROCARBONS BY COPPER (I) COMPLEXES

BACKGROUND OF THE INVENTION

This invention relates to the removal and recovery of unsaturated hydrocarbons from feedstreams. More particularly, alkenes of alkynes are removed from feedstreams by formation of a complex with Cu(I)-fluorinated acetylacetonate, in the presence of a stabilizing agent which prevents disproportionation of the complex to copper metal during recovery of alkene or alkyne.

It is well-known that cuprous salt solutions will absorb carbon monoxide (CO). A review of the early literature relating to this topic may be found in J. Appl. Chem. (London), 15, 17–28(1965). It is also known that certain silver(I) and copper(I) salts form complexes with olefins and acetylenes. For example, cuprous chloride is known to form complexes with both ethylene and acetylene. U.S. Pat. No. 3,401,112 teaches a method of separating a mixture of hydrocarbons having differing degrees of unsaturation using a copper(I) salt of the formula CuXA where XA is an anion, X is oxygen or fluorine and A is the remainder of the anion. Examples of fluorinated anions include fluoro substituted carboxylates, fluorosulphonate, perfluoroborate, hexafluorophosphate and hexafluoroantimonate. CuXA forms a cuprous complex with said unsaturated hydrocarbon. Similarly, U.S. Pat. No. 3,517,079 describes a process for separating vinyl aromatic hydrocarbons from alkyl aromatic hydrocarbons using a cuprous fluoroborate or cuprous fluorophosphate salt wherein a complex is formed. U.S. Pat. Nos. 3,754,047 and 3,755,487 relate to a process for separating complexible ligands such as olefins, acetylenes, aromatics and CO from a feedstream using cuprous salts such as $CuAlCl_4$, $CuBF_4$, $CuOOCCF_3$, $CuPF_6$ and the like. A process for separating CO from gas mixtures using copper(I) salts of sulfonic acids or dialkyl phosphates is disclosed in U.S. Pat. No. 4,042,669. U.S. Pat. No. 4,048,292 teaches a method for preparing high purity CO from $CO_2$-free gas streams using a copper ammonium $C_1$–$C_2$ acetate as the absorbent medium. Inorganic Chemistry, 11, 2840 (1972) teaches the preparation of Ag(I) complexes containing hexafluoroacetylacetonate and olefins. The preparation occurs in an aqueous medium using soluble Ag(I) salts. Finally, U.S. Pat. No. 4,279,874 describes a process for removing CO from a gas stream wherein the gas stream is contacted with an absorbent solution containing a Cu(I) complex with halogenated beta-diketonate as ligand thereby removing CO as a carbonyl-Cu(I)-halogenated beta-diketonate complex.

The known processes for removing CO or olefins by Cu(I) complex formation suffer from one or more disadvantages such as high corrosivity, low reactivity to CO, high energy cost to regenerate CO, low selectivity to CO, instability of the absorbent system and formation of Cu metal during regeneration of absorbent solution. It would be highly desirable to have a method for selectivity and efficiently removing unsaturated hydrocarbon from a feedstream while at the same time being able to regenerate the absorbent system under mild conditions without formation of copper metal.

SUMMARY OF THE INVENTION

It has been discovered that alkenes or alkynes can be selectively absorbed from feedstreams using Cu(I) salts and the Cu(I)-containing absorbent regenerated without depositing metal from solution. Accordingly, there is provided a process for separating alkene, alkyne or mixture thereof from a feedstream without copper metal formation which comprises the steps of:

(a) contacting the feedstream with a solution of a cuprous fluorinated acetylacetonate of the formula

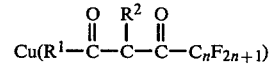

where $R^1$ is $C_1$–$C_6$ fluoroalkyl, $C_1$–$C_8$ alkyl, $C_4$–$C_6$ heterocycle containing O, S or N or $C_6$–$C_{10}$ aryl, $R^2$ is H or $C_1$–$C_6$ alkyl with the proviso that $R^1$ and $R^2$ together with the carbons to which they are attached may be joined together to form a $C_6$ ring, and n is an integer from 1 to 8, in an organic solvent containing a stabilizing agent at a temperature sufficient to remove at least one of alkene or alkyne by forming a first Cu(I) complex of the formula

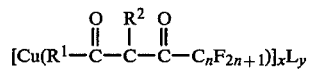

where $R^1$, $R^2$ and n are defined above, x and y are 1 or 2, and L is alkene or alkyne, said stabilizing agent being characterized by replacing L in the first Cu(I) complex thereby forming a second Cu(I) complex which is stable at temperatures wherein the first Cu(I) complex decomposes through loss of alkene or alkyne, (b) heating the resulting mixture to a temperature sufficient to decompose the first Cu(I) complex through loss of alkene or alkyne whereby the stabilizing agent replaces alkene or alkyne is said first Cu(I) complex and copper metal formation is prevented by formation of the second Cu(I) complex, and (c) separating the displaced alkene, alkyne or mixture thereof.

Another embodiment of the invention for separating alkenes, alkynes or mixtures thereof from feedstreams without copper metal formation comprises the steps of:

(a) contacting the feedstream with a solution of a cuprous fluorinated acetylacetone of the formula

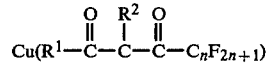

where $R^1$ is $C_1$–$C_6$ fluoroalkyl, $C_1$–$C_8$ alkyl, $C_4$–$C_6$ heterocycle containing O, S or N or $C_6$–$C_{10}$ aryl, $R^2$ is H or $C_1$–$C_6$ alkyl with the proviso that $R^1$ and $R^2$ together with the carbons to which they are attached may be joined together to form a $C_6$ ring, and n is an integer from 1 to 8, in an organic solvent containing a stabilizing agent at a temperature sufficient to remove at least one of alkene or alkyne by forming a Cu(I) complex of the formula

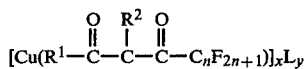

where $R^1$, $R^2$ and n are defined above, x and y are 1 or 2, and L is alkene or alkyne, said stabilizing agent being characterized by replacing L in the first Cu(I) complex thereby forming a second Cu(I) complex which is stable at temperatures wherein the first Cu(I) complex decomposes through loss of alkene or alkyne, (b) reducing pressure by an amount sufficient to decompose the first Cu(I) complex through loss of alkene or alkyne whereby the stabilizing agent replaces L in the first Cu(I) complex and copper metal formation is prevented by formation of the second Cu(I) complex; and (c) separating the alkene, alkyne or mixture thereof.

A further embodiment of the invention for separating alkenes, alkynes or mixtures thereof from feedstreams without copper metal formation comprises the steps of:

(a) contacting the feedstream with a solution of a cuprous fluorinated acetylacetonate of the formula

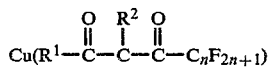

where $R^1$ is $C_1-C_6$ fluoroalkyl, $C_1-C_8$ alkyl, $C_4-C_6$ heterocycle containing O, S or N or $C_6-C_{10}$ aryl, $R^2$ is H or $C_1-C_6$ alkyl with the proviso that $R^1$ and $R^2$ together with the carbons to which they are attached may be joined together to form a $C_6$ ring, and n is an integer from 1 to 8, in a organic solvent containing a stabilizing agent at a temperature sufficient to remove at least one of alkene or alkyne by forming a Cu(I) complex of the formula

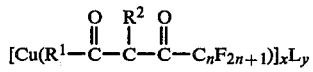

where $R^1$, $R^2$ and n are defined above, x and y are 1 or 2, and L is alkene or alkyne, said stabilizing agent being characterized by replacing L in the first Cu(I) complex thereby forming a second Cu(I) complex which is stable at temperatures wherein the first Cu(I) complex decomposes through loss of alkene or alkyne, (b) adding an inert gas stripping agent in an amount sufficient to strip L from the first Cu(I) complex whereby the stabilizing agent replaces L in the first Cu(I) complex and copper metal formation is prevented by formation of the second Cu(I) complex; and (c) separating the alkene, alkyne or mixture thereof.

When Cu(I) beta-diketonate complexes containing alkenes or alkynes as ligands are decomposed to remove ligand without the presence of a stabilizing agent, a disproportionation reaction occurs producing copper metal and a Cu(II) salt. Processing these mixtures involves the handling of slurries containing copper metal which is disadvantageous due to difficulties presented by such slurries. The present invention avoids this problem during heating by maintaining the Cu(I) in solution as a stabilized complex.

DETAILED DESCRIPTION OF THE INVENTION

When a feedstream containing alkene, alkyne or mixture thereof is contacted with cuprous fluorinated acetylacetonate solution in an organic solvent, a first cuprous complex is formed as illustrated by the following reaction:

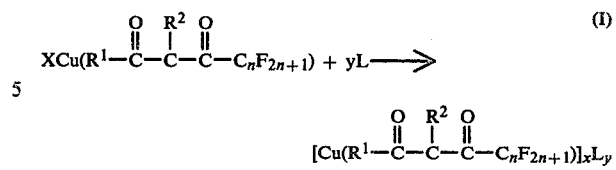

where $R^1$, $R^2$ and n are defined as above, x and y are 1 or 2 and L is alkene or alkyne.

In order to separate L, the cuprous complex product of reaction (I) is heated and an equilibrium is established, i.e.,

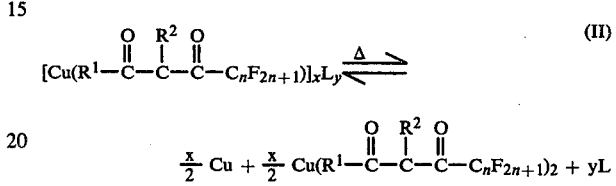

The present invention is direced to avoiding reaction (II) and this is accomplished by adding a stabilizing agent thus maintaining the cuprous complex in solution as a second cuprous complex as shown below.

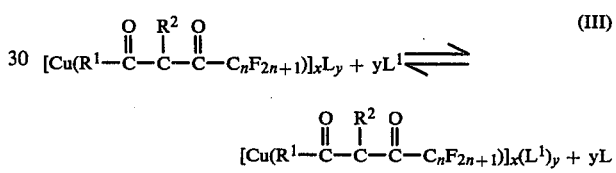

During decomposition of the first cuprous complex by heating, pressure reduction or inert gas stripping, the more volatile ligand L is driven off while the less volatile stabilizing agent $L^1$ replaces L in the first cuprous complex thus forcing the equilibrium in favor of the more stable second cuprous complex containing $L^1$. The equilibrium of reaction (III), in a heating-cooling reaction cycle, can be shifted in the reverse direction by lowering the temperature and contacting with fresh feedstream which results in reformation of

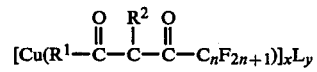

which is thermodynamically more stable at lower temperatures and $L^1$ is displaced. This heating-cooling, pressure reduction or inert gas stripping reaction cycle can be repeated without any noticeable formation of solids, particularly Cu metal.

It is possible for any given alkene or alkyne to function as either L or $L^1$ in reactions (I) and (III) above. The selection of $L^1$ is dependent on the nature of L in the feedstream, and is based on the stability of the first cuprous complex formed in reaction (I) above. One measure of complex stability is the decomposition temperature. This can be estimated by conventional methods. For example, a sample of solution containing the first Cu(I)-L complex from reaction (I) can be heated in a temperature-controlled infrared cell and infrared spectral changes recorded as a function of temperature. Alternatively, the Cu(I)-L complex can be isolated from solution, and the resultant solid heated. Decomposition temperatures are estimated by observing the partial pressure of L as a function of temperature. The decomposition temperature of the second Cu(I) complex described in reaction (III) above should be at least 5° C., preferably from 10° C. to 150° C., and especially from 50° C. to 100° C. greater than the decomposition temperature of the first Cu(I) complex.

As noted above, any given alkene or alkyne may be either L or $L^1$. Preferred alkenes and alkynes are (a) alkenes of the formula:

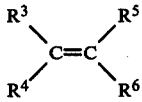

where each $R^3$-$R^6$ is independently H provided that for $L^1$, at least one of $R^3$-$R^6$ in $L^1$ is not H; $C_1$-$C_{30}$, more preferably $C_1$-$C_{15}$ and especially $C_1$-$C_8$ aliphatic with the proviso that any combination of $R^3$, $R^4$, $R^5$ and $R^6$ may be joined together to form at least one $C_4$-$C_{14}$, more preferably $C_5$-$C_{12}$, most preferably $C_6$-$C_8$ cycloaliphatic ring; —C≡N; $C_6$-$C_{10}$ aryl; $C_7$-$C_{14}$ araliphatic;

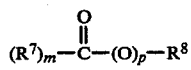

where m and p are 0 or 1, $R^7$ is $C_1$-$C_{20}$, preferably $C_1$-$C_{10}$ aliphatic, and $R^8$ is H, $C_1$-$C_{10}$ aliphatic or $C_6$-$C_{10}$ aryl with the proviso that adjacent

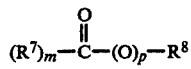

may be joined together to form a $C_4$-$C_{16}$ anhydride; and (b) alkynes of the formula $R^9$—C≡C—$R^{10}$ where $R^9$ and $R^{10}$ are independently H; $C_1$-$C_{30}$, more preferably $C_1$-$C_{15}$ and especially $C_1$-$C_8$ aliphatic; $C_6$-$C_{10}$ aryl or $C_7$-$C_{14}$ araliphatic. Stabilizing agents may also be isonitriles, nitriles and sulfides of the respective formulae $R^{11}$—N C, $R^{12}$—C≡N and $R^{13}$—S—$R^{14}$ where $R^{11}$ to $R^{14}$ are independently $C_1$-$C_{20}$, preferably $C_1$-$C_{10}$ aliphatic; $C_3$-$C_{10}$, preferably $C_5$-$C_7$ cycloaliphatic; $C_7$-$C_{20}$, preferably $C_7$-$C_{14}$ araliphatic or $C_6$-$C_{10}$ aryl. Preferred L include $C_2$-$C_{10}$, especially $C_2$-$C_6$ alkenes and alkynes. More preferred stabilizing agents are $C_4$-$C_{30}$, especially $C_5$-$C_{20}$ and particularly $C_6$-$C_{14}$ alkenes, alkynes and isonitriles. The aliphatic, cycloaliphatic, araliphatic and aryl hydrocarbyl radicals may be substituted with unreactive substituents such as halogen, alkoxy, nitro and the like, and the aliphatic, cycloaliphatic or araliphatic hydrocarbyl radicals may be saturated or unsaturated.

Examples of suitable alkenes and alkynes include: ethylene, acetylene, 1-octene, isobutylene, 1,5-cyclooctadiene, stilbene, diphenylacetylene, 1-dodecene, styrene, cyclooctene, 1,5,9-cyclododecatriene, 1,3-hexadiene, isopropylacetylene, 1-decene, 1-tetradecene, 1,5-bicycloheptadiene, 1-octadecene, cyclopentene, octalin, methylene cyclohexane, diphenyl fulvene, 1-octadecyne, benzyl cinnamate, benzal acetophenone, acrolein, acrylonitrile, maleic anhydride, oleic acid, linolenic acid, acrylic acid, methyl methacrylate and diethyl maleate. Suitable isontriles, nitriles and sulfide are, e.g., methyl isocyanide, butyl isocyanide, cyclohexyl isocyanide, phenylethyl isocyanide, phenyl isocyanide, acetonitrile, propionitrile, benzonitrile, cyclohexylnitrile, benzylnitrile, diethyl sulfide, di-n-butylsulfide, diphenylsulfide, dibenzylsulfide, and methyl butyl sulfide.

Cuprous complexes containing L and $L^1$ are exemplified by:
Cu(1,5-cyclooctadiene)(hfacac),
(hfacac=1,1,1,5,5,5-hexafluoroacetylacetonate),
Cu(ethylene)(hfacac),
$Cu_2$(bicyclo[2.2.1]hepta-2,5-diene)(hfacac)$_2$,
Cu(isoprene)(hfacac),
Cu(1-decene)(hfacac),
Cu(diethylmaleate)(hfacac),
Cu(styrene)(hfacac),
Cu(1,3-butadiene)(hfacac),
Cu(diphenylacetylene)$_2$(hfacac),
$Cu_2$(2,8-decadiyne)(hfacac)$_2$,
Cu(2-hexyne)(hfacac),
$Cu_2$(1,3,5,7-cyclooctatetraene)(trifluoroacetylacetonate)$_2$
and Cu(1,5-cyclooctadiene)(thenoyltrifluoroacetylacetonate)

Cuprous fluorinated acetylacetonate solutions are preferably prepared by reacting $Cu_2O$ and fluorinated acetylacetone in an organic solvent. Such solutions may be prepared, however, by other methods such as the reaction of a Cu(I) salt with thallium fluorinated acetylacetonate salt in an organic solvent. If stabilizing agent is used as the organic solvent, a secondary reaction will occur in which the second cuprous complex containing $L^1$ will be formed. This has no effect on removing L from feedstream since L will displace $L^1$ at lower temperatures due to thermodynamic considerations as noted herein.

Preferred fluorinated acetylacetone ligands which are reacted to form cuprous fluorinated acetylacetonates have the formula

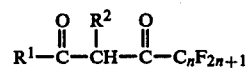

where $R^1$ is $C_1$-$C_3$ fluoroalkyl, especially $CF_3$, $C_1$-$C_8$ alkyl which may be substituted with phenyl, $C_6$-$C_{10}$ aryl or $C_4$-$C_5$ heterocycle containing O, S or N, especially S, $R^2$ is H with the proviso that $R^1$ and $R^2$ may join together to form a $C_6$ ring and n is 1 to 4, especially 1. Examples of preferred embodiments of fluorinated acetylacetonates include

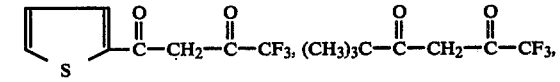

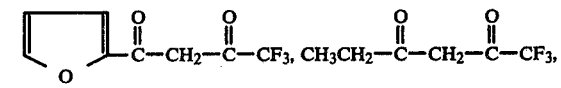

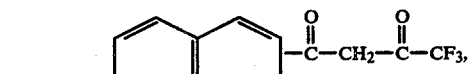

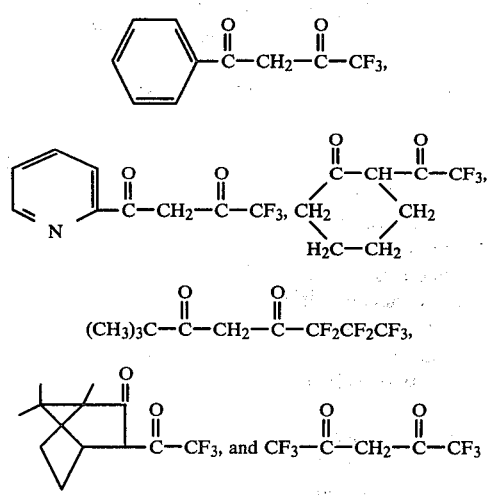

is especially preferred.

The process of the invention takes place in an organic solvent. Said solvents may be inert solvents such as ethers, ketones, esters, alcohols, saturated aliphatic hydrocarbons, aromatic hydrocarbons and the like, or they may be the stabilizing agents used as $L^1$ in reaction (III) above. It is preferred to use the stabilizing agent $L^1$ as the organic solvent because this minimizes separations problems. It is also desirable to carry out the process in an inert atmosphere since substantial amounts of oxidizing gases such as oxygen may result in the undesirable conversion of Cu(I) to Cu(II). If an inert organic solvent is employed, stabilizng agent may be present during the preparation of cuprous fluorinated acetylacetonate solution, or stabilizing agent may be added after formation of first cuprous complex pursuant to reaction (I) above. Stabilizing agent must, however, be present before decomposition of said first cuprous complex.

Reaction times are not critical, and feedstream is contacted with cuprous fluorinated acetylacetonate solution for a sufficient time to remove alkene, alkyne or mixture thereof. Feedstreams may be easily monitored using gas or liquid chromatography for detecting removal of desired components.

For reaction (I) above, wherein the L component is being removed from feedstream by reaction with cuprous fluorinated acetylacetonate solution to form a first cuprous complex, the temperature is that sufficient to remove L. The preferred operating temperature for this step of the process of the invention is a function of the stability of the cuprous complex. For example, complexes such as Cu(ethylene)(hfacac) have relatively high vapor pressures and therefore lower temperatures, e.g. 0°–30° C. are desirable. On the other hand, when L is a higher boiling alkene such as 1-hexene, a more stable cuprous complex is formed and hence higher operating temperatures may be employed without decomposing the cuprous complex. To determine the preferred operating temperature for any given L, the reaction temperature is raised or lowered and the feedstream monitored to determine removal of L. The most preferred operating temperature is the maximum temperature wherein L is completely removed. This maximizes kinetic factors without causing Cu(I) complex decomposition.

Decomposition of the initially formed first cuprous complex is exemplified by reaction (III) above and requires forcing the equilibrium of reaction (III) in favor of the second Cu(I) complex of the formula

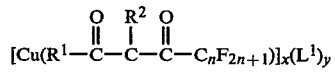

This may be accomplished by heat, pressure reduction or inert gas stripping.

In the case of temperature, the first Cu(I) complex formed according to reaction (I) above is heated to its decomposition temperature in the presence of stabilizing agent $L^1$. Decomposition occurs pursuant to reaction (III) and $L^1$ replaces L in the second Cu(I) complex which is stable at the above-mentioned decomposition temperature. Upon separating L and lowering the temperature below the decomposition temperature, fresh feedstream is added thereby reversing the equilibrium of reaction (III) by forming additional first Cu(I) complex which is thermodynamically more stable at lower temperatures.

Pressure differentials may also be employed to decompose the first Cu(I) complex through loss of L. In one embodiment, the pressure of the reaction system is reduced by an amount sufficient to cause decomposition and loss of L whereby $L^1$ replaces L to form a second Cu(I) complex having a substantially lower vapor pressure at any given temperature. The amount of pressure reduction is not critical although the greater the pressure reduction, the more rapid the decomposition. Lower pressure limits are influenced by the vapor pressure of organic solvent. In the case where stabilizing agent is the organic solvent, it is preferred to use a stabilizing agent having a high boiling point and low vapor pressure so as to minimize any solvent loss at reduced pressure. In another embodiment, an inert gas stripping agent such as $N_2$, $CH_4$, noble gas and the like is used to flush the first Cu(I) complex-containing solution thereby causing loss of L by reducing the overall partial pressure of L in the system. As above, $L^1$ replaces L to form the second Cu(I) complex having a substantially lower vapor pressure. Repressurizing, if necessary, and adding fresh feedstream reverses reaction (III) by reforming the first Cu(I) complex which is more stable in the presence of excess L.

Complexes having relatively high L vapor pressure may employ any of the individual decomposition means described above. A more stable complex such as Cu(1-hexene)(hfacac) may require a combination of heat and pressure reduction or inert gas stripping.

Wide variations in concentration of cuprous fluorinated acetylacetonate in the reaction mixture are possible depending on the concentration of L, i.e., alkene, alkyne or mixture thereof in the feedstream. It is preferred to maintain cuprous fluorinated acetylacetonate in an amount equal to or less than the stoichiometric amount required by the concentration of L in the feedstream, and a slight deficiency, i.e., 0.1 to 10% is especially preferred. The concentration of less volatile $L^1$ used is not critical and may range from an amount equivalent to the concentration of Cu(fluorinated acetylacetonate)L complex in solution in the reaction mixture to a very large excess. $L^1$ preferably serves as the organic solvent.

While the process of the invention may be carried out in a batchwise or continuous mode, a continuous mode of operation is preferred. Feedstream containing L is contacted with a reaction mixture of cuprous fluorinated acetylacetonate in organic solvent containing stabilizng agent in a stirred reaction vessel. Upon completion of removal of L from feedstream, the temperature is raised, pressure reduced or inert gas stripping agent added to facilitate displacement of L by $L^1$ in the first cuprous complex. If L is a normally gaseous alkene or alkyne, the resulting gas is separated, the reaction vessel cooled, if elevated temperatures are employed, and fresh feedstream introduced into the reaction vessel. For liquid feedstreams, L is separated from reaction mixture. The system should be repressurized on adding fresh feedstream if reduced pressures are employed. It is also desirable to separate feedstreams components from the reaction mixture using known techniques, e.g., fractional distillation before adding fresh reactants to the reaction vessel.

The gas and/or liquid feedstreams may contain other inert gases such as $N_2$, $H_2$, $CO_2$, alkanes, water vapor, as well as mixtures of inert organic solvents. $H_2S$, $SO_2$, $SO_3$ and $O_2$ should not, however, be present in amounts greater than about 10 vol%.

The invention is further illustrated by the following examples.

EXAMPLE 1

A solution of Cu(ethylene)(hfacac) was prepared from 10 mmoles $Cu_2O$, 20 mmoles hexafluoroacetylacetone (hfacac) and 75 ml tetrahydrofuran (THF) by bubbling ethylene through the solution for 20 minutes at which time the reaction was complete. Twenty mmoles of cyclooctene was added to the mixture and the solution was then heated to 40° C. for one hour. Infrared analysis showed that the ethylene was completely removed by this treatment. A ethylene mixture was then passed through the solution at 25° C. for 20 minutes and the infrared spectra indicated that the ethylene complex had been restored to its original concentration. Heating to 40° again caused the ethylene to be displaced. This sequence was repeated several times without any noticable formation of copper metal or other solids.

EXAMPLE 2

A solution of Cu(ethylene)(hfacac) in diethylmaleate was prepared in the same manner as described in Example 1 except that diethyl maleate was used as the solvent instead of THF. The solution, with heating to 50° C. for 30 minutes, lost all of its bound ethylene. On cooling to room temperature and passing a gas mixture containing ethylene and nitrogen through the solution for 20 minutes, the ethylene complex was restored to its original concentration. The process was repeated several times without any deposition of copper metal or other solids.

EXAMPLE 3

The procedure of Example 2 was repeated except that 40 mmoles $Cu_2O$, 80 mmoles hexafluoroacetylacetone and 50 ml α-pinene were used as reactants. This solution contained approximately 8 wt. % Cu and had a higher capacity for ethylene than the diethylmaleate solutions. The absorption cycle was repeated several times without copper deposition.

EXAMPLE 4

The procedure of Example 2 was repeated except that the solution was prepared from 80 mmoles $Cu_2O$, 160 mmole hexafluoroacetylacetone and and 50 ml 2,4,4-trimethyl-1-pentene. This solution contained greater than 13 percent copper and was also stable after several absorption cycles.

EXAMPLE 5

This example was identical to Example 2 except that the gas mixture consisted of propylene and nitrogen. A Cu(propylene)(hfacac) complex formed illustrating that higher olefins can also be removed from mixtures by these complexes. No Cu metal deposition was observed upon further absorption cycles.

EXAMPLE 7

This example was identical to Example 5 except the gas mixture consisted of 2-butyne and nitrogen. This experiment demonstrates the feasibility of separating alkynes from inert gases.

EXAMPLE 8

A solution of Cu(ethylene)(hfacac) in diethyl maleate was prepared in the same manner as described in Example 2. The solution containing the ethylene complex was then subjected to a vacuum (the absolute pressure was approximately 0.1 atm) for one hour. During this time the solution lost almost all of the bound ethylene. A gas mixture containing ethylene and hydrogen was then passed through the solution for 20 minutes restoring the ethylene complex to its original concentration. This process was continued through several more cycles without any noticeable formation of copper metal.

EXAMPLE 9

A solution of Cu(ethylene)(hfacac) in diethylmaleate was prepared in the same manner as described in Example 2. A rapid stream of nitrogen was passed through this solution for two hours which almost entirely stripped the bound ethylene from the solution. A gas stream containing ethylene and hydrogen was then passed through the solution for 40 minutes restoring the ethylene complex to its original concentration. This process was repeated without any deposition of copper metal.

COMPARATIVE EXAMPLE

A solution of Cu(ethylene)(hfacac) in dichloromethane was prepared from 10 mmoles $Cu_2O$, 20 mmoles hexafluoroacetylacetone and 75 ml $CH_2Cl_2$ by bubbling an ethylene-nitrogen mixture through the solution for 20 minutes at which time all the solid $Cu_2O$ had dissolved and the reaction was complete. A rapid stream of nitrogen was then passed through the solution liberating the ethylene. After the reaction was complete the solution had turned deep green with a large quantity of metallic copper deposited. This illustrates that in the absence of a stabilizing agent, copper deposition takes place on ethylene separation pursuant to reaction (II) hereinbefore.

What is claimed is:

1. A process for separating alkene, alkyne or mixture thereof from a feedstream without copper metal formation which comprises the steps of:
    (a) contacting the feedstream with a solution of a cuprous fluorinated acetylacetonate of the formula

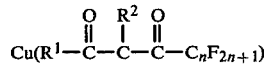

where $R^1$ is $C_1$-$C_6$ fluoroalkyl, $C_1$-$C_8$ alkyl, $C_4$-$C_6$ heretocycle containing O, S, or N or $C_6$-$C_{10}$ aryl, $R^2$ is H or $C_1$-$C_6$ alkyl with the proviso that $R^1$ and $R^2$ together with the carbons to which they are attached may be joined together to form a $C_6$ ring and n is an integer from 1 to 8, in an organic solvent containing a stabilizing agent at a temperature sufficient to remove at least one of alkene or alkyne by forming a Cu(I) complex of the formula

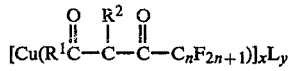

where $R^1$, $R^2$ and n are defined above, x and y are 1 or 2, and L is alkene or alkyne, said stabilizing agent being characterized by replacing L in the first Cu(I) complex thereby forming a second Cu(I) complex which is stable at temperatures wherein the first Cu(I) complex decomposes through loss of alkene or alkyne, (b) heating the resulting mixture to a temperature sufficient to decompose the first Cu(I) complex through loss of alkene or alkyne whereby the stabilizing agent replaces alkene or alkyne in said first Cu(I) complex and copper metal formation is prevented by formation of the second Cu(I) complex, and (c) separating the alkene, alkyne or mixture thereof.

2. A process for separating alkenes, alkynes or mixtures thereof from feedstreams without copper metal formation comprises the steps of:

(a) contacting the feedstream with a solution of a cuprous fluorinated acetylacetonate of the formula

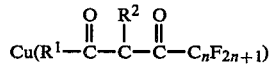

where $R^1$ is $C_1$-$C_6$ fluoroalkyl, $C_1$-$C_8$ alkyl, $C_4$-$C_6$ heretocycle containing O, S, or N or $C_6$-$C_{10}$ aryl, $R^2$ is H or $C_1$-$C_6$ alkyl with the proviso that $R^1$ and $R^2$ together with the carbons to which they are attached may be joined together to form a $C_6$ ring and n is an integer from 1 to 8, in an organic solvent containing a stabilizing agent at a temperature sufficient to remove at least one of alkene or alkyne by forming a Cu(I) complex of the formula

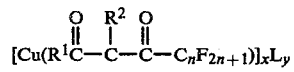

where $R^1$, $R^2$ and n are defined above, x and y are 1 or 2, and L is alkene or alkyne, said stabilizing agent being characterized by replacing L in the first Cu(I) complex thereby forming a second Cu(I) complex which is stable at temperatures wherein the first Cu(I) complex decomposes through loss of alkene or alkyne, (b) reducing pressure by an amount sufficient to decompose the first Cu(I) complex through loss of alkene or alkyne whereby the stabilizing agent replaces L in the first Cu(I) complex and copper metal formation is prevented by formation of the second Cu(I) complex, and (c) separating the alkene, alkyne or mixture thereof.

3. A process for separating alkenes, alkynes or mixtures thereof from feedstreams without copper metal formation comprises the steps of:

(a) contacting the feedstream with a solution of a cuprous fluorinated acetylacetonate of the formula

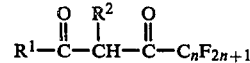

where $R^1$ is $C_1$-$C_6$ fluoroalkyl, $C_1$-$C_8$ alkyl, $C_4$-$C_6$ heretocycle containing O, S, or N or $C_6$-$C_{10}$ aryl, $R^2$ is H or $C_1$-$C_6$ alkyl with the proviso that $R^1$ and $R^2$ together with the carbons to which they are attached may be joined together to form a $C_6$ ring and n is an integer from 1 to 8, in an organic solvent containing a stabilizing agent at a temperature sufficient to remove at least one of alkene or alkyne by forming a Cu(I) complex of the formula

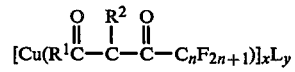

where $R^1$, $R^2$ and n are defined above, x and y are 1 or 2, and L is alkene or alkyne, said stabilizing agent being characterized by replacing L in the first Cu(I) complex thereby forming a second Cu(I) complex which is stable at temperatures wherein the first Cu(I) complex decomposes through loss of alkene or alkyne, (b) adding an inert gas stripping agent in an amount sufficient to strip L from the first Cu(I) complex whereby the stabilizing agent replaces L in the first Cu(I) complex and copper metal formation is prevented by formation of the second Cu(I) complex, and (c) separating the alkene, alkyne or mixture thereof.

4. The process of claim 1 wherein after separating alkene, alkyne or mixture thereof, the reaction mixture is cooled and fresh feedstream is added thereby displacing stabilizing agent from the second Cu(I) complex by reforming the first Cu(I) complex.

5. The process of claim 1, 2 or 3 wherein the stabilizing agent is an alkene, alkyne, isonitrile, nitrile or sulfide.

6. The process of claim 1, 2 or 3 wherein L and the stabilizing agent are alkenes of the formula $R^3R^4C$=$CR^5R^6$ where each $R^3$-$R^6$ is independently H provided that at least one of $R^3$-$R^6$ in $L^1$ is not H; $C_1$-$C_{30}$ aliphatic with the proviso that any combination of $R^3$, $R^4$, $R^5$ and $R^6$ may be joined together to form at least one $C_4$-$C_{14}$ cycloaliphatic ring; —C≡N; $C_6$-$C_{10}$ aryl; $C_7$-$C_{14}$ araliphatic;

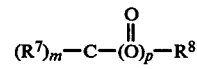

where m and p are 0 or 1, $R^7$ is $C_1$-$C_{20}$ aliphatic, and $R^8$ is H, $C_1$-$C_{10}$ aliphatic or $C_6$-$C_{10}$ aryl with the proviso that adjacent

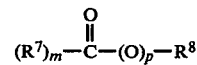

may be joined together to form a $C_4$-$C_{16}$ anhydride.

7. The process of claim 1, 2 or 3 wherein L or the stabilizing agents are alkynes of the formula $R^9$—C C—$R^{10}$ where $R^9$ and $R^{10}$ are independently H; $C_1$-$C_{30}$ aliphatic; $C_6$-$C_{10}$ aryl or $C_7$-$C_{14}$ araliphatic.

8. The process of claim 1, 2 or 3 wherein the stabilizing agents are isonitriles, nitriles or sulfides of the respective formulae $R^{11}$—N≡C, $R^{12}$—C≡N or $R^{13}$—S—$R^{14}$ where $R^{11}$ to $R^{14}$ are independently $C_1$-$C_{20}$ aliphatic, $C_3$-$C_{10}$ cycloaliphatic, $C_7$-$C_{20}$ araliphatic or $C_6$-$C_{10}$ aryl.

9. The process of claim 1, 2 or 3 wherein $R^1$ is $CF_3$, $C_1$-$C_8$ alkyl which may be substituted with phenyl, $C_6$-$C_{10}$ aryl or $C_4$-$C_5$ heterocycle containing S, $R^2$ is H with the proviso that $R^1$ and $R^2$ may be joined together to form a $C_6$ ring, and n is 1.

10. The process of claim 1, 2 or 3 wherein the fluorinated acetylacetone is hexafluoroacetylacetone.

11. The process of claim 1, 2 or 3 wherein the stabilizing agent is also the organic solvent.

12. The process of claim 2 or 3 wherein after separating L, fresh feedstream is added whereby $L^1$ is displaced from the second Cu(I) complex and L is removed from fresh feedstream by reforming the first Cu(I) complex.

* * * * *